United States Patent [19]
Ellner

[11] Patent Number: 4,767,932
[45] Date of Patent: Aug. 30, 1988

[54] ULTRAVIOLET PURIFICATION DEVICE

[75] Inventor: Sidney Ellner, Bedford, N.Y.

[73] Assignee: Ultraviolet Purification System, Inc., Bedford Hills, N.Y.

[21] Appl. No.: 911,716

[22] Filed: Sep. 26, 1986

[51] Int. Cl.4 .......................................... G01N 21/01
[52] U.S. Cl. .................................. 250/435; 250/436; 422/24
[58] Field of Search .................. 250/432 R, 435, 436; 422/24

[56] References Cited

U.S. PATENT DOCUMENTS

| | | | |
|---|---|---|---|
| 3,462,597 | 8/1969 | Young | 422/24 |
| 4,204,956 | 5/1980 | Flatow | 422/24 |
| 4,255,663 | 3/1981 | Lewis | 250/436 |
| 4,367,410 | 1/1983 | Wood | 250/436 |
| 4,482,809 | 11/1984 | Maarschalkerweerd | 250/435 |

Primary Examiner—Bruce C. Anderson
Attorney, Agent, or Firm—Arthur T. Fattibene

[57] ABSTRACT

An ultraviolet purification device for irradiating liquids with ultraviolet radiation either in an open system or a closed system which includes a frame or vessel provided with a header plate and a spaced apart support grid for supporting therebetween a plurality of quartz jackets. Each jacket is provided with an open end which extends beyond the header plate and in which one or more ultraviolet lamps are disposed in tamdem therein. The arrangement is such that the respective lamps are disposed in rows or banks wherein the respective rows or banks can be independently energized depending upon the flow rate of the liquid. Each lamp is constructed so that the electrical contacts for the respective lamp electrodes project from a common end of the lamp, thereby permitting the lamps to be inserted from one side of the frame or vessel. An improved spacer is also provided for spacially supporting each lamp within its respective jacket.

18 Claims, 3 Drawing Sheets

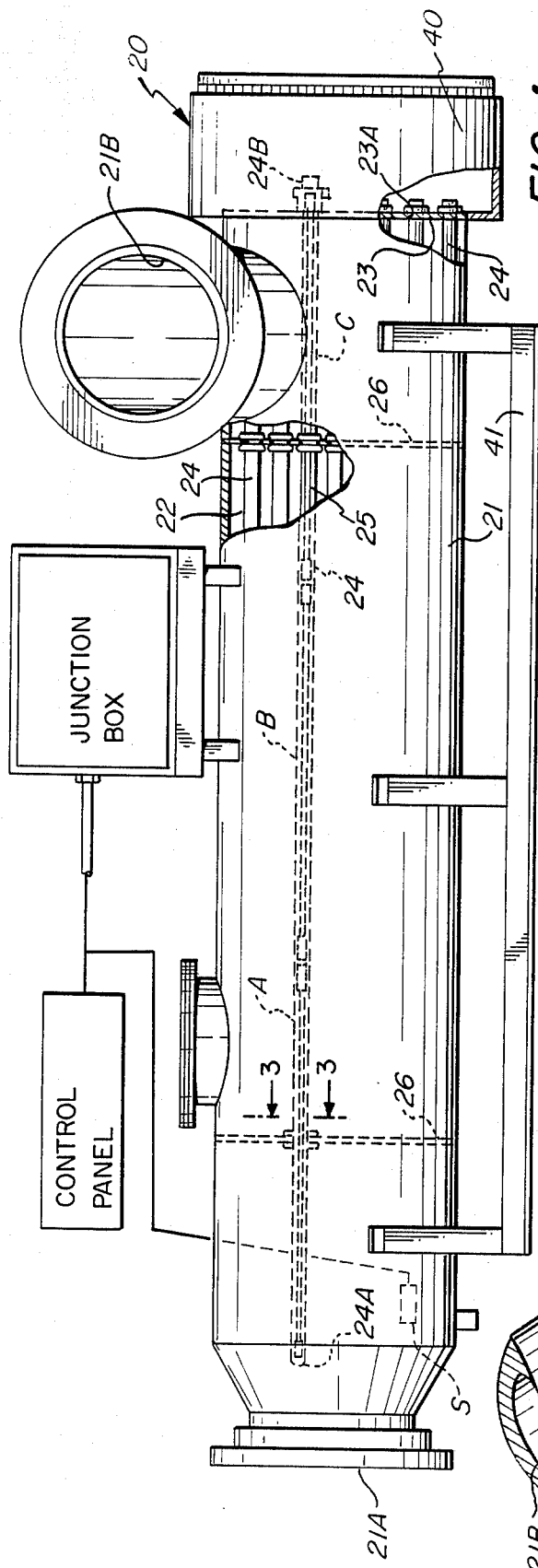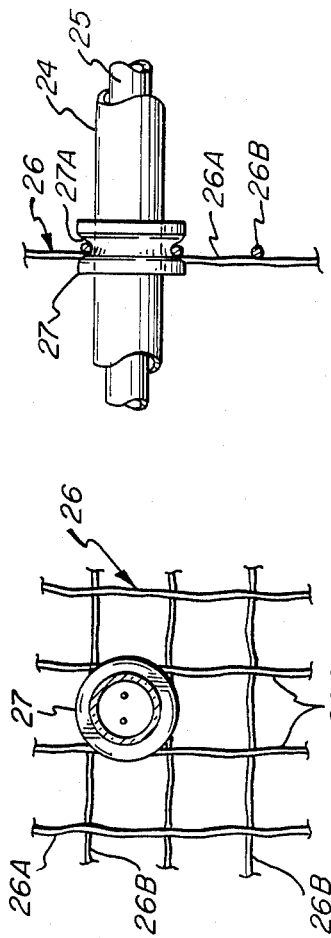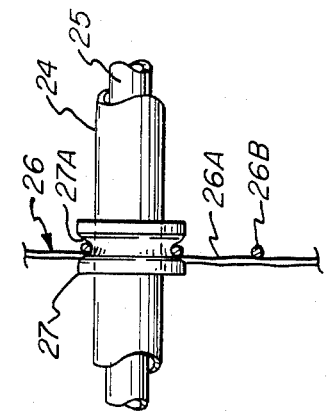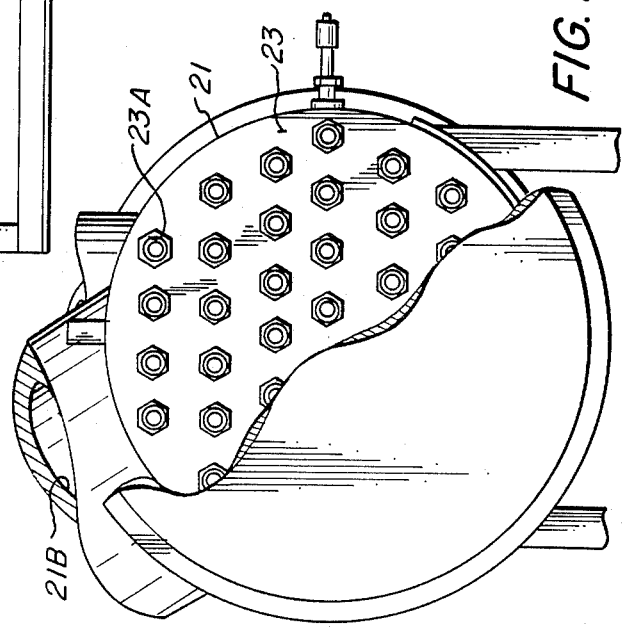

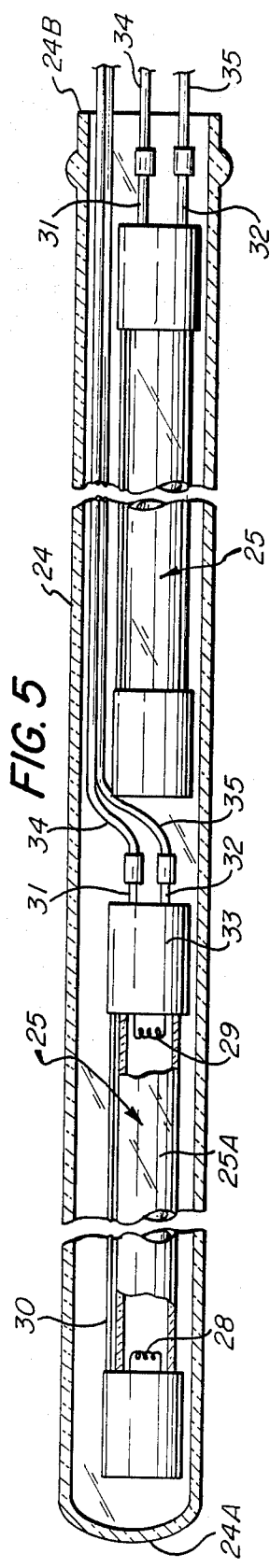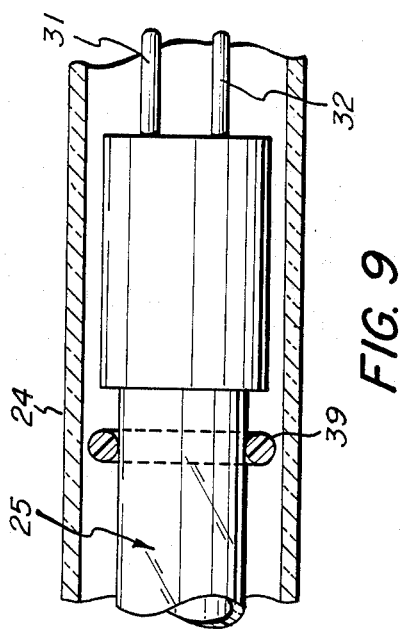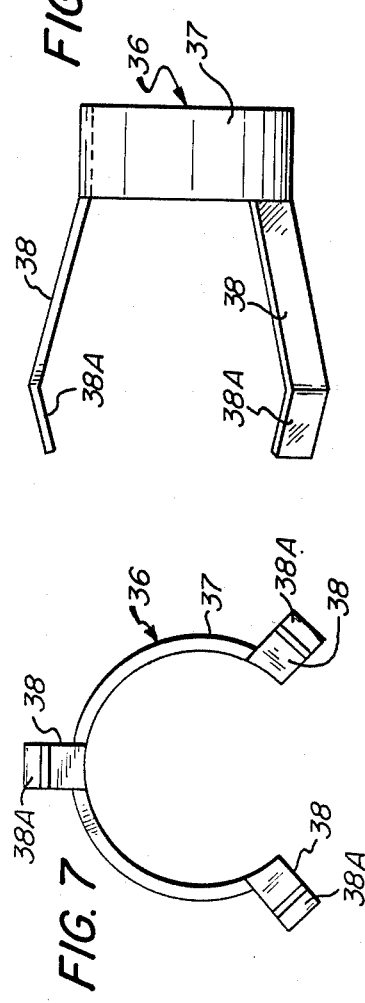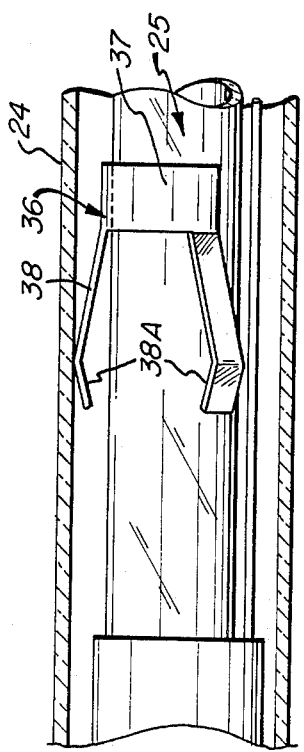

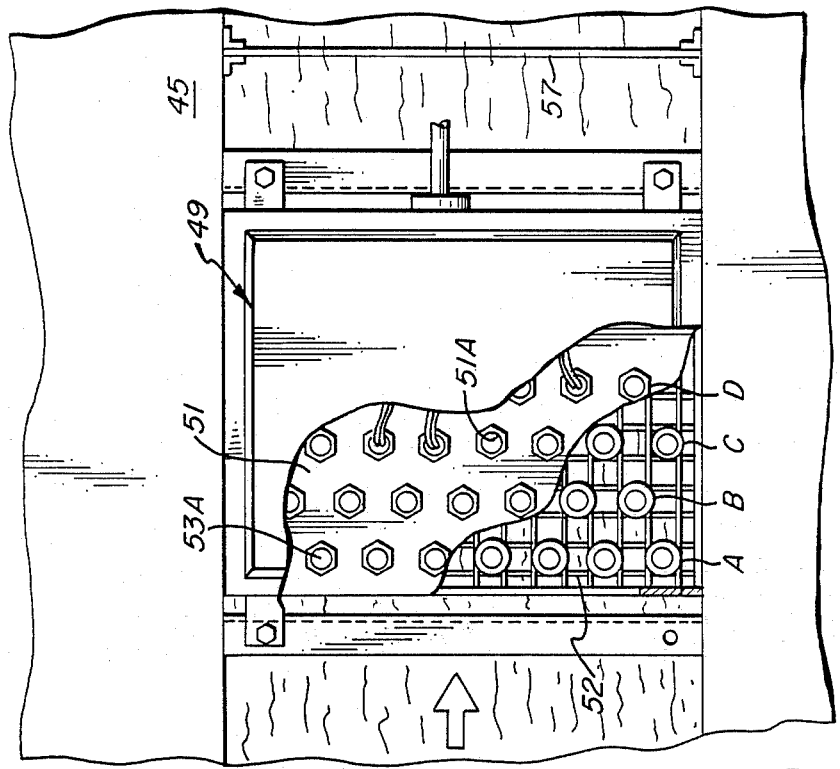
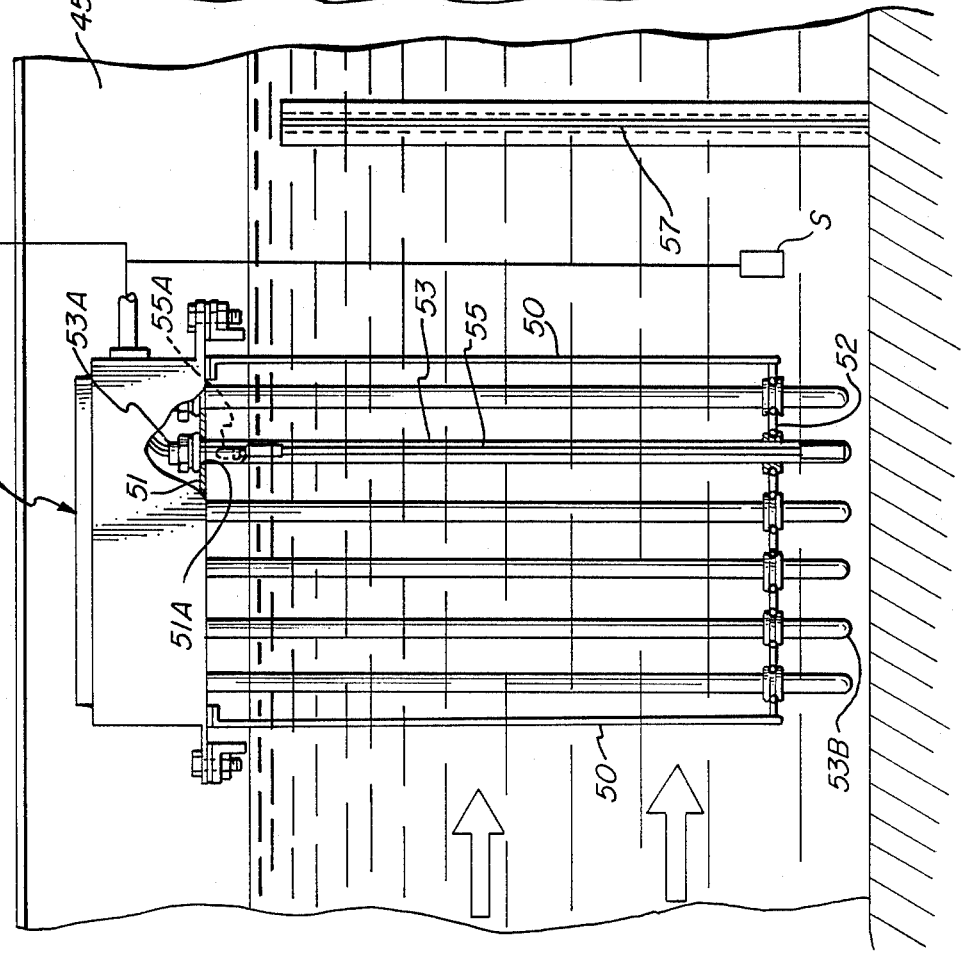

ULTRAVIOLET PURIFICATION DEVICE

FIELD OF INVENTION

This invention is directed to an ultraviolet purification system or device for large scale application in which one or more ultraviolet lamps are disposed in tamdem to define one or more rows or banks of lamps whereby the rows or banks can be independently actuated in accordance with the rate of liquid flow, and which lamps can be readily removed or replaced from one end of the device.

PROBLEM AND PRIOR ART

The use of ultraviolet radiation to destroy microorganisms and/or to effect purification of air or liquid is well known, and various known devices exist for such purposes. Such known devices are disclosed in my prior U.S. Pat. No. 4,103,167; and in other patented publications such as Canadian Pat. No. 1,163,086, U.S. Pat. Nos. 4,296,328; 3,923,663 and 1,140,819.

Heretofore, the conventionally known types of ultraviolet germicidal or purification system or devices generally comprised a chamber having a number of ultraviolet lamps disposed in quartz tubes requiring electrical connections on both ends of the lamp for applying germicidal radiation to a liquid flowing through the chamber. Such chambers have been formed with spaced apart headers for supporting the quartz jackets therebetween, and which quartz jackets were required to be opened at each end and sealed at its respective ends to the opposed spaced end headers. This was primarily due to the fact that the standard germicidal or ultraviolet lamp required electrical connections at both ends. For this reason, the length of the contact chamber was generally determined by the length of the ultraviolet lamp. To utilize such chambers to treat relatively large flow rates, the diameter of the chamber had to be increased in order to accommodate the additional number of lamps to satisfactorily effect the purification of such readily large flow rates. Thus as the diameter of the contact chamber is increased relative to the fixed length as determined by the length of the ultraviolet lamp, the ratio of chamber diameter to length increases to result in undesirable hydraulic flow patterns. Also, with such described vessels, the fluid inlet and outlet were angularly disposed relative to the lamps which resulted in a cross flow pattern that induced undesirable stresses on the lamp assembly.

OBJECTS

An object of this invention is to provide ultraviolet purification unit in which the length of the contact chamber is not dependent or determined by the length of a conventional ultraviolet lamp.

Another object is to provide an ultraviolet purification device in which a plurality of lamp banks are disposed in tamdem to more effectively and efficiently handle large varying flow rates.

Another object of this invention is to provide an ultraviolet contact chamber having a minimum of hydraulic headloss.

Another object is to provide an ultraviolet contact chamber which is constructed so as to minimize vibration and strain on the quartz jackets at high linear velocities.

Another object is to provide an ultraviolet purification device with an arrangement capable of varying the delivery of sufficient ultraviolet radiation in accordance with the flow rate of the liquid therethrough.

Another object is to provide an ultraviolet purification device with a plurality of lamp banks arranged so that all the available contact areas receive an adequate amount of ultraviolet radiation even if one or more banks of lamps are turned off.

Another object is to provide for an ultraviolet purification device having a lamp bank construction whereby the electrical connections are not submerged in the liquid being treated.

Another object is to provide a purification device wherein the germicidal lamps can be readily removed and/or replaced without removing the unit out of contact with the liquid being treated.

SUMMARY OF THE INVENTION

The foregoing objects and other features and advantages are attained by a purification device which includes a vessel defining an elongated closed contract chamber, one end of which defines an inlet for introducing the liquid to be treated longitudinally of the chamber. The other end of the chamber is closed by a header plate having a series of holes formed therein for receiving a plurality of quartz jackets. Spaced from the header plate are one or more grid supports for supporing therebetween the elongated quartz jackets. An outlet is disposed in communication with the chamber adjacent the header plate. The respective quartz jackets comprise elongated clear tubes having the upstream end thereof sealed and the opened downstream end thereof projecting through a corresponding jacket hole formed in the header plate so that the jacket open end projects slightly beyond the header plate. In accordance with this invention, the elongated jackets are of a length to receive two or more germicidal or ultraviolet lamps in tamdem therein. The respective lamps include an elongated sealed envelope having an electrode disposed at each end of the envelope with the contact terminals located at a common end of the envelope as taught in my jointly filed co-pending patent application Ser. No. 699,088, filed Feb. 7, 1985, now U.S. Pat. No. 4,700,101. The described lamp construction enables a plurality of lamps to be serially inserted in tamdem into each of the respected quartz jackets so that all of the electrical connections can be made at one end of the vessel only. The arrangement also provides for a plurality of tamdem lamp banks to be formed within the chamber whereby the number of lamps can be substantially increased to effectively treat large volume of liquid without increasing the diameter of the chamber. The respective lamp banks are wired in a control circuit whereby each bank can be independently energized in accordance to the volume or flow rate of liquid through the chamber. Spring spacers are detachably connected to the respective lamps for maintaining the lamps spacially disposed within their respective jackets.

Another form of the invention is directed to a purification device which can be readily placed in an open purification channel. In this form, the device includes a header plate and a spaced apart support grip for supporting therebetween a plurality of quartz jackets which are arranged in a plurality of rows wherein the jackets in one row are staggered relative to the jackets disposed in an adjacent row. Connected to the header plate is an access housing into which the open end of the jackets extend. Disposed in each of the respective jackets is a germicidal or ultraviolet lamp of the type hereinbefore described so that all electrical connections and/or access to the quartz jackets can be had at one end. The respective rows of lamps can be wired into banks of one or more rows so that each bank can be independently actuated depending upon the flow rate of the liquid therethrough.

FEATURES

A feature of this invention resides in ultraviolet purification device in which plurality of ultraviolet lamps are disposed in tamdem within a quartz jacket so that the respective lamps can be removed or replaced from end thereof.

Another feature of this invention resides in the provision whereby the number of lamps in a contact chamber can be substantially increased without the attendance increase in chamber diameter.

Another feature resides in the provision of an ultraviolet purification device which can effectively and efficiently operate over a relatively wide range of flow rates.

Another feature resides in the provision of an improved spacer for maintaining the lamps spacially disposed within its respective jackets.

Other features and advantages will become more readily apparant when considered in view of the drawings and specification in which:

FIG. 1 is a side view of a purification device embodying the invention with parts broken away.

FIG. 2 is a right end view of FIG. 1 having parts broken away.

FIG. 3 is a fragmentary sectional detail taken along line 3—3 on FIG. 1.

FIG. 4 is a side view showing of FIG. 3.

FIG. 5 is a sectional side view of the lamp assembly in accordance with this invention.

FIG. 6 is a detail side view of a spring spacer utilized in the invention.

FIG. 7 is an end view of the spacer of FIG. 6.

FIG. 8 is a fragmentary sectional side view of a detail of construction.

FIG. 9 is a sectional detail side view of another spacer arrangement.

FIG. 10 is a side view of a modified form of the invention.

FIG. 11 is a top plan view of the embodiment of FIG. 10.

DETAILED DESCRIPTION

Referring to the drawings there is shown in FIG. 1 an ultraviolet purification system 20 embodying the invention. As shown the purification system includes an elongated vessel 21 to define a purification chamber 22 through which a liquid to be purified flows. The vessel 21 includes an inlet 21A through which the liquid is introduced for longitudinal fluid flow therethrough. The treated fluid exits through outlet 21B. The end of the vessel 21 opposite the inlet is closed by a header plate 23 which is provided with a series of holes 23A for accommodating the free end of the quartz jackets 24 which contain the ultraviolet lamps 25, as will be hereinafter described. It will be understood that the open ends of the jackets 24 are extended through the header plate in a fluid tight manner. Longitudinally spaced from the header plate 23 are one or more support grids 26, depending upon the length of the vessel. In the illustrated embodiment of FIG. 1 at least two such support grids are shown. As best seen in FIGS. 3 & 4, the support grid 26 may comprise a lattice type grid defined by a series of vertical and transverse wire rods 26A & 26B that are interlaced to define a plurality support openings or grid squares adapted to be disposed in alignment with the opening or holes 23A in the header plate 23. As shown in FIG. 1 the support grids 26 extend transversely of the chamber 22.

In accordance with this invention a plurality of clear quartz jackets 24 defined as elongated tubes extend longitudinally of the vessel. In the illustrated embodiment of FIG. 1, the downstream end 24A of each jacket is closed. The upstream end 24B of the jackets 24 which extends through the header plate 23 is open.

To minimize vibration a gromlet 27 is fitted to the grid square through which the jacket is extended as best seen in FIGS. 3 & 4. Preferrably the gromlet is formed of Teflon or other UV resistant material. As seen in FIG. 4 the gromlet 27 is provided with a circumscribing groove 27A to provide a seat for frictionally receiving the adjacent vertical and transverse wire rods 26A and 26B whereby the gromlet 27 can be snap fitted and retained in place to the grid square.

A plurality of germicidal or ultraviolet lamps 25 are inserted through the open end 24B of the quartz jackets so as to be serially disposed in tamdem therein. As best seen in FIG. 5 each lamp 25 comprises a glass envelope 25A which is sealed by the opposed ends thereof. An electrode 28 and 29 is disposed in each end of the lamp. An insulated wire conductor 30 connects electrode 28 to a terminal contact 31. Electrode 29 is electrically connected to contact 32. As seen the terminal contacts 31 and 32 for the respective electrodes extend from a common end 33 of the lamp 25. The respective terminal contacts 33 and 32 are in turn connected into a suitable circuit by leads 34 and 35 which extend outwardly through the open end 24B of the jacket. Each lamp disposed in tamdem within a common jacket are similarly constructed. With the construction described it will be apparent that the respective lamps can be readily inserted and/or removed from the jacket 24 from the open end 24B thereof. In the form of the invention disclosed in FIG. 1, three lamps are disposed in tamdem within each jacket. However, it will be understood that the length of the vessel may be such as to accommodate more or less than three lamps shown depending upon the flow capacity of an installation in which the purification unit is intended to be used.

The arrangement described thus defines a plurality of lamp banks, e.g. A, B & C as illustrated in FIG. 1 that are disposed in tamdem within the vessel 21. Each lamp bank A, B & C defines an array of lamps that are spaced within the circumference of the vessel so as to provide the optimum spacing therebetween for effecting the optimum exposure of the fluid or liquid flowing therethrough to the generated ultraviolet radiation produced by each bank. The wire leads 34, 35 of the lamps comprising lamp banks A, B & C are suitably connected in a circuit whereby each bank A, B or C can be separately and/or simultaneously enerized. Thus depending upon the flow rate of the liquid flowing through the chamber 22, one or more banks A, B or C may be enerized so as to generate the required amount of ultraviolet radiation to treat the given volume of liquid flowing therethrough. With the arrangement described, low flow rate may require only one bank be energized. For maximum flow rate, all the banks may be energized. Thus it will be noted that regardless of the flow rate, all areas or spaces are receiving the optimum amount of ultraviolet radiation. A suitable flow meter may be incorporated in the lamp circuit whereby the respective banks A, B & C can be automatically turned on or off depending upon the volume or flow rate of the liquid to be treated.

To minimize stress of vibration and to resiliently maintain the respective lamp 25 in spacial relationship within their respective jackets 24, a resilient spacer 36 is provided. Referring to FIGS. 6, 7 & 8 the resilient spacer 36 comprises a resilient split ring or collar 37 which is adapted to be snap fitted about the lamp 25. Projecting laterally and circumferentially spaced about the circumference of the collar 37 are a plurality of resilient or spring fingers 38. As shown the respective spring fingers are flexed outwardly in a manner to exert a normally outwardly bias so that in operation, the respective spring finger 38 maintains the lamp 25 spacially disposed within the jacket 24 as seen in FIG. 8. By positioning at least two such spacers 36 on each lamp at longitudinal spaced intervals, the lamp can be resiliently maintained in spaced relationship within its respective jacket. As shown, the free end 38A of each finger is slighly bent inwardly which functions to facilitate the insertion of the lamp into its elongated jacket 24. FIG. 7 illustrate another type of spacer 39 which may be also useful in maintaining the spacing of the lamp 25 within its jacket 24. In this form the spacer 39 may comprise a Teflon O-ring which is fitted to the lamp body or envelope.

Completing the assembly of the purification device or system 20 is an access housing 40 which circumscribes the end of the vessel whereby access is provided for effecting the replacement, insertion and/or maintenance of the respective lamps and associated jackets. If desired, the vessel 21 is provided with a suitable base or strand 41.

FIGS. 10 and 11 illustrate an ultraviolet purification system or unit which is particularly adapted for ultraviolet purification of liquids flowing through open channels, weirs and the like 45. In the illustrated embodiment of FIGS. 10 and 11 the unit or device 49 comprises a frame means 50 formed of suitable structural members to which an upper header plate 51 and a lower support grid 52 are disposed in a predetermined spacial relationship. The header plate 51 is provided with a plurality of rows of spaced header openings 51A to receive the open ends 53A of a quartz jacket 53 in a manner similar to that hereinbefore described. The lower end 53B of the respective jackets 53 are closed and are supported in the lower grid 52 in a similar manner as described with respect to FIGS. 3 & 4. Enclosing the upper end or header plate 51 is a suitable access housing 54 wherein the electrical connection and circuit components are contained. Disposed in each of its jackets 53 are one or more ultraviolet lamps 55 which are similiarly constructed to lamps 25 hereinbefore described. Because the lamps 55 have the electrode contacts projecting from the upper common end 55A of the respective lamps 55, the respective lamps 55 can be readily serviced from the top of the unit 49 without the need of effecting the removal of the unit 49 from the fluid being treated, and thereby the treatment need not be interrupted for effecting lamp replacement or repair. The specific construction of the lamp 55 also enables all electrical connections and circuit components to be disposed above the level of the fluid or liquid being treated, and thus obviate potential shock hazzards inherent in units rquiring submerged electrical parts.

As shown in FIG. 11, the jacket holes 53A formed in the header plate are arranged so that the header holes 53A disposed in one row are staggered relative to the header holes 53A disposed in the next adjacent row. The staggered array thus creates an unulating fluid flow of the liquid in flowing through the respective rows of ultraviolet lamps to effect maximum contact with the ultraviolet energy generated by the lamps 55.

As previously described, lamps 55 are resiliently spaced within their respective jackets by spacer 36 or 39 as hereinbefore described.

It will be understood that the rows of lamps 55 may be wired into one or more banks of lamps whereby the respective banks can be independently energized in accordance to flow rate or volume to be treated. For example, rows A & B of lamps 55 may comprise one bank of lamps and rows C and D may comprise another bank of lamps, and so on. In this manner only those banks of lamps need be energized which are necessary to effect purification of a given volume or rate of flow. Generally such open channels or weirs are provided with a gate or lock 57 whereby the rate of flow can be controlled.

With the construction described it will be noted that no submerged electrical connections are required. The replacement of lamps can be readily effected from only one end of the unit or device. The respective lamps do not require relatively costly and complex water or liquid tight connections, nor is the purification treatment interrupted to effect lamp replacement. In the systems described the respective banks of lamps can be effectively turned on and off in a controlled manner and in proportion to the rate or volume of flow and still allow for complete purification of the given fluid flow, and thereby result in substantial savings of energy costs.

While the invention has been described with respect to several embodiments thereof, variations and modifications may be made without departing from the spirit or scope of the invention.

What is claimed is:

1. An ultraviolet purification system for irradiating liquids with ultraviolet radiation comprising,
   a means for channeling the liquid to be treated,
   a source of ultraviolet radiation disposed in said channeling means,
   said source of ultraviolet radiation including,
   at least one jacket disposed in fluid flow relationship to the liquid to be treated,
   said jacket being opened at one end and closed at the other end thereof, said open end being sealed off from the liquid to be treated, and said closed end being disposed in the free flow of the liquid to be treated,
   an ultraviolet lamp disposed in said jacket,
   said lamp comprising a glass envelope having an electrode disposed at each end of said glass envelope,
   an electrical conductor electrically connected to the electrode remotely disposed relative to the open end of the jacket containing said lamp,
   said electrical conductor being sufficiently long to extend to the other end of said lamp,
   a source of electrical energy,
   and means for connecting said lamp in circuit with said electrical energy source whereby the lamp can be readily replaced from said open end of said jacket.

2. An ultraviolet purification unit comprising, a means defining an ultraviolet contact chamber,
said chamber having a fluid inlet and a fluid outlet,
means defining an access header disposed at one end of said chamber,
a support grid disposed within said chamber and spaced from said header,
an elongated tubular jacket supported between said grid and said header,
said jacket having an open end which extends outwardly of said header, and having its other end closed, said closed end being disposed axially relative to said fluid inlet, and in the free flow of the liquid to be treated,
at least one ultraviolet lamp disposed within said jacket,
said lamp having an electrode disposed adjacent the opposed ends thereof,
terminal contacts electrically connected to each of said electrodes, said terminal contacts being disposed at one end of said lamp only, nearest to said open end of the jacket,
and electrical conductors electrically connected to said terminal contacts,
said electrical conductors being sufficiently long so as to extend beyond the open end of the lamp jacket whereby said conductors are adapted to connect to a source of electrical energy.

3. An ultraviolet purification unit as defined in claim 2 wherein the length of said chamber comprises a multiple of the length of said lamp.

4. An ultraviolet purification unit comprising,
a means defining an ultraviolet contact chamber,
said chamber having a fluid inlet and a fluid outlet,
means defining an access header disposed at one end of said chamber,
a support grid disposed within said chamber and spaced from said header,
a plurality of elongated tubular jackets supported between said grid and said header,
each of said jackets having an open end which extends outwardly of said header,
a plurality of ultraviolet lamps disposed in end to end relationship within each of said jackets,
each of said lamps having an electrode disposed adjacent the opposed ends thereof,
terminal contacts electrically connected to each of said electrodes, said terminal contacts being disposed at one end of said lamps only,
and electrical conductors electrically connected to said terminal contacts,
said electrical conductors being sufficiently long so as to extend beyond the open end of the corresponding lamps jacket whereby said conductors are adapted to connect to a source of electrical energy,
and including spacer means for maintaining said lamps spacially disposed within its respective jacket, said spacer means including,
a C shaped resilient collar adapted to be snap fitted to said lamp, and
a plurality spring fingers extending from said collar,
said spring fingers extending radially outwardly of said collar for exerting a spring bias against the inner surface of said jacket,
and said spring fingers being circumferentially spaced about said collar for spacially supporting said lamp within its jacket.

5. An ultraviolet purification unit as defined in claim 4 wherein said spacer means is formed of metal.

6. An ultraviolet purification unit comprising,
an elongated vessel defining a contact chamber,
means defining a fluid inlet at one end of said vessel,
and a header plate disposed adjacent the other end of said elongated vessel,
said header plate having a plurality of openings formed therein,
a support grid disposed within said vessel and spaced from said header plate,
and a plurality of elongated quartz jackets supported between said header plate and said grid,
each of said quartz jackets being closed at one end and opened at the other end, said open end being extended beyond said header plate, and said closed end being disposed in alignment with said fluid inlet and in free flow relationship to the fluid to be treated,
means defining a fluid outlet adjacent said header plate whereby the fluid flow through said contact chamber is generally parallel to said jackets,
a plurality of ultraviolet lamps disposed in tandem in each of said jackets, whereby said lamps define a plurality of lamp banks corresponding in number to the number of lamps disposed in each jacket,
control means for actuating said lamps banks whereby said lamp banks can be independently energized in accordance with the rate of flow through said contact chamber.

7. An ultraviolet purification unit as defined in claim 6 wherein each of said lamps comprises,
an elongated glass envelope,
an electrode disposed at each end of said envelope,
terminal contacts electrically connected to each of said electrodes being disposed at one end only of said lamps,
electrical conductors connected to said terminal contacts,
said electrical conductors being sufficiently long as to project through the open end of said jacket, so that the lamps disposed in alignment in each of said jackets can be readily removed and/or inserted through the open end of said jackets which are commonly disposed at one end of said vessel.

8. An ultraviolet purification unit as defined in claim 7 wherein the lamp electrode remote from the open end of said jacket is electrically connected to its respective contact terminal by a wire conductor disposed externally of its respective lamp envelope.

9. An ultraviolet purification unit as defined in claim 8, and including a spring clip connected to said lamp for maintaining said lamp spacially disposed within its respective jacket.

10. An ultraviolet purification unit as defined in claim 9, wherein said spring clip comprises a C-shaped collar adapted to snap fit about said lamp, and a plurality of spring fingers extending laterally of said collar, said fingers being circumferencially spaced about said collar, and said spring fingers having their respective free ends biased radially outwardly for maintaining the lamp spacially disposed within its respective jacket.

11. An ultraviolet purification unit for irradiating a liquid flowing through a channel with ultraviolet radiation comprising,
a frame including an upper header plate and a lower supporting grid spaced therefrom,
a plurality of quartz jackets interconnected between said header plate and said grid, said jackets being disposed in spaced apart rows wherein the jackets in one row are staggered relative to the jackets in an adjacent row, said jackets being closed at one end and opened at its other end, said open end projecting beyond said header plate, and said closed end being disposed in free flow to the liquid being treated, an elongated ultraviolet lamp disposed in each of said jackets, each of said lamps comprising an elongated glass envelope, an electrode disposed in each end of said envelope, a terminal contact electrically connected to each of said electrodes, said terminal contact for each electrode projecting from a common end of said lamps, said common end of said lamps being remotely disposed relative to the closed end of its respective jacket, and a control means for controlling the actuation of each of lamps whereby each lamp row may be independently energized in accordance with the rate of liquid flow.

12. An ultraviolet purification unit as defined in claim 11 and including a housing circumscribing said header plate, and means defining an access opening to said housing whereby all of the lamps can be readily removed and replaced without removing the unit from the liquid 13. An ultraviolet purification unit for effecting ultraviolet purification of fluids flowing through open channels comprising a frame defining an upper header plate and a lower support grid, structural member for maintaining said header plate and support grid in fixed predetermined aligned spacial relationship, a plurality of elongated jackets disposed between said header plate and said grid, said jacket having an open end portion which extends through said header plate, said jacket having a closed lower end, said closed lower end being in free flow relationship to the liquid being tested, an ultraviolet lamp disposed in each of said jackets, each of said lamps including a glass envelope, an electrode disposed at each end of said glass envelope, an electrical conductor connected to the electrode that is remotely disposed relative to the open end of said jacket, said electrical conductor being sufficiently long so as to extend the length of the lamp toward the open end of said jacket whereby said lamps can be readily replaced from the open end of said jackets, and said elongated jackets being readily submersible in the fluid to be treated.

14. A purification unit as defined in claim 13 wherein said lamp includes a terminal connected electrically to each of said electrodes, and said terminal connected for each of said electrode project outwardly from a common end of said lamp.

15. A purification unit as defined in claim 14 wherein said lamps are arrayed in a plurality of banks whereby each of said bands are independently actuated whereby one or more banks can be energized relative to the fluid flow passing therethrough.

16. An ultraviolet purification unit as defined in claim 15 and including a housing encasing said header plate, means defining a source of electrical energy, and a control means for operating said banks of lamps whereby said banks are energized in accordance to the rate of flow of the fluid to be treated; each of said banks extending transversely of said open channel.

17. An ultraviolet purification means as defined in claim 13 and including resilient spacer means for maintaining said lamps in spacial relationship relative its respective jacket.

18. An ultraviolet purification system for irradiating liquids with ultraviolet radiation as defined in claim 1 and including resilient spacer means for maintaining said lamp spacially disposed within its respective jacket, said spacer means including a collar adapted to be snap fitted to said lamp, and a plurality of spring fingers extending from said collar, said fingers being circumferentially spaced about said collar for spacially supporting said lamp within said jacket.

* * * * *